(12) United States Patent
Siccardi et al.

(10) Patent No.: US 11,717,332 B2
(45) Date of Patent: Aug. 8, 2023

(54) SURGICAL DEVICE

(71) Applicant: MEDACTA INTERNATIONAL SA, Castel San Pietro (CH)

(72) Inventors: Francesco Siccardi, Castel San Pietro (CH); Meinrad Fiechter, Castel San Pietro (CH); Marco Riva, Castel San Pietro (CH); Marco Rampon, Castel San Pietro (CH)

(73) Assignee: MEDACTA INTERNATIONAL SA, Casiel San Pietro (CH)

( * ) Notice: Subject to any disclaimer, the term of this patent is extended or adjusted under 35 U.S.C. 154(b) by 0 days.

(21) Appl. No.: 17/602,220

(22) PCT Filed: Apr. 8, 2020

(86) PCT No.: PCT/IB2020/053338
§ 371 (c)(1),
(2) Date: Oct. 7, 2021

(87) PCT Pub. No.: WO2020/208536
PCT Pub. Date: Oct. 15, 2020

(65) Prior Publication Data
US 2022/0142682 A1 May 12, 2022

(30) Foreign Application Priority Data
Apr. 8, 2019 (IT) .................. 102019000005358

(51) Int. Cl.
*A61B 17/70* (2006.01)
*A61B 17/88* (2006.01)
*A61B 90/00* (2016.01)

(52) U.S. Cl.
CPC .......... *A61B 17/7085* (2013.01); *A61B 90/03* (2016.02); *A61B 2090/037* (2016.02)

(58) Field of Classification Search
CPC .............. A61B 17/708; A61B 17/7077; A61B 17/7082; A61B 17/7083; A61B 17/7085;
(Continued)

(56) References Cited

U.S. PATENT DOCUMENTS 9,907,582 B1 3/2018 Olea
10,159,579 B1 12/2018 Reitblat et al.
(Continued)

FOREIGN PATENT DOCUMENTS

| JP | 2013144115 A | 7/2013 |
|---|---|---|
| JP | 201513106 A | 1/2015 |

(Continued)

OTHER PUBLICATIONS

International Search Report and Written Opinion issued in PCT/IB2020/053338, dated Aug. 7, 2020, 13 Pages.
(Continued)

*Primary Examiner* — Eduardo C Robert
*Assistant Examiner* — David C Comstock
(74) *Attorney, Agent, or Firm* — Meunier Carlin & Curfman LLC

(57) ABSTRACT

A surgical device includes a polyaxial surgical screw that includes an internally hollow tulip. The tulip includes two elongated rods which are parallel and mutually spaced apart, each elongated rod protruding from a side wall of the tulip and extending away from a first end of the tulip in a direction opposite to a second end of the tulip. The rods define a channel in communication with the first end for accessing the interior of the tulip. A locking unit can be reversibly mounted on the polyaxial surgical screw. The locking unit includes a tubular body which has an inner cavity and is adapted to be fitted about the elongated rods during a configuration of use of the surgical device. The tubular body has two mutually opposite protrusions which project into the inner cavity that are configured to face the channel and be mutually interposed.

8 Claims, 4 Drawing Sheets

(58) Field of Classification Search
CPC ............ A61B 17/7086; A61B 17/7032; A61B 17/7035; A61B 17/7037; A61B 17/7038; A61B 17/7034; A61B 17/7079; A61B 17/7076; A61B 90/04; A61B 2090/037
USPC ........................................ 606/104.86 A, 279
See application file for complete search history.

(56) References Cited

U.S. PATENT DOCUMENTS

| 2010/0114179 | A1* | 5/2010 | Moore ............... A61B 17/7085 606/86 A |
| 2013/0096635 | A1 | 4/2013 | Wall |
| 2013/0245705 | A1 | 9/2013 | McBride et al. |
| 2015/0173803 | A1* | 6/2015 | Droulout ............ A61B 17/7037 606/266 |
| 2016/0113685 | A1 | 4/2016 | Ishii et al. |

FOREIGN PATENT DOCUMENTS

| JP | 2017127551 A | 7/2017 |
| WO | 2007149426 A2 | 12/2007 |
| WO | 2017027694 A1 | 2/2017 |

OTHER PUBLICATIONS

English Translation of Notice of Reasons of Refusal in JP 2021-559392, dated Aug. 19, 2022, 13 pages.

Notice of Decision of Refusal with English translation, issued in connection with Japanese Application No. 2021-559392, dated Mar. 15, 2023, 5 pages.

\* cited by examiner

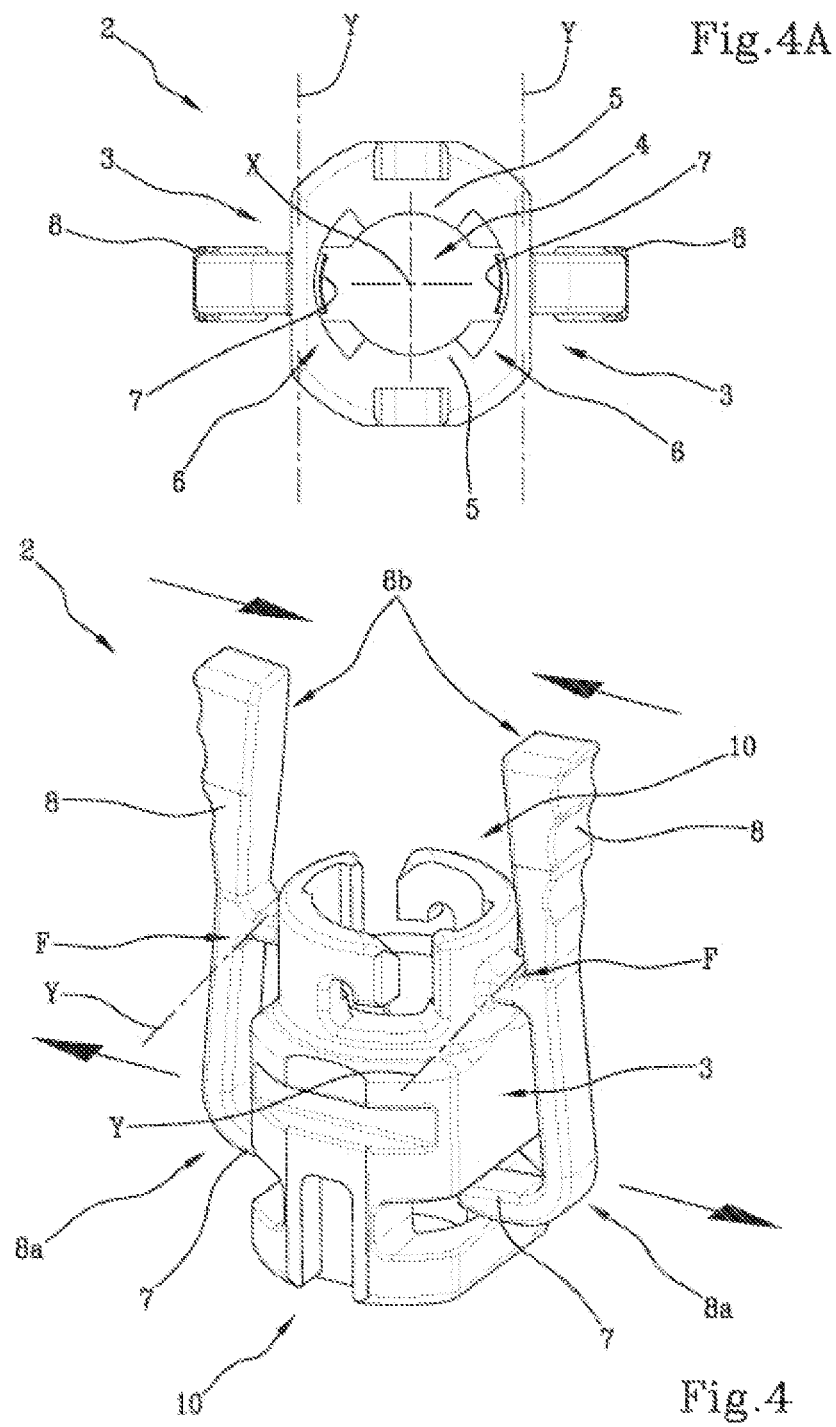

SURGICAL DEVICE

TECHNICAL FIELD

The present invention relates to a surgical device for implanting a polyaxial surgical screw.

BACKGROUND ART

It is known that spinal surgery often requires the stabilization of a portion of the spinal tract to facilitate the fusion of two or more vertebrae into a single bone agglomeration.

This type of operation is frequently used to correct many pathological conditions of the spinal column, such as degenerative diseases of the disc elements, scoliosis, spinal stenosis or the like.

These corrective interventions mostly require the use of implants, such as bone grafts in particular. The stabilization of the spinal column allows the creation of bone tissue in the intervertebral area; in this manner, part of the spinal column is fused into a single bone body.

The stabilization of the spinal column has been studied at length in the past and various methods and devices have been developed for the correction of many diseases which are characteristic of this anatomical part to stabilize its configuration and facilitate vertebral fusion at various levels.

One of these known systems includes a bar to be placed longitudinally along the tract of the spine which requires the operation. This bar is shaped to represent the correct anatomical shape which is typical of a healthy tract of the spinal column.

Therefore, with this method, the bar is positioned along the spinal column to engage various vertebrae, as needed. It is worth noting that two parallel bars arranged on the sides of the central area of the spinal column are typically used in this type of surgery. Therefore, during these surgeries, the pair of bars is fixed to the spinal column by various means, comprising, for example, screws properly fixed to the bone structure, typically to the vertebral pedicle.

The inclination of the bar, and therefore the positioning of the fixing screws, varies according to the type of correction to be imposed and obviously varies from vertebra to vertebra. It is apparent that correctly fixing both the corrective bar and the screws to which it will be fixed is essential for the success of the operation.

For correctly positioning said elements, according to the patient's needs, polyaxial screws are used, which are therefore able to work along transversal axes and not coincide with the development axis of the screw itself.

To reduce the invasiveness of the polyaxial screws and bar implantation operations, surgical technique has now turned towards minimally invasive techniques capable of considerably reducing tissue trauma, with benefits for the patient, e.g. such as less time spent in hospital, less post-surgery pain, shorter rehabilitation, and for hospital facilities, i.e. less time spent in hospital, lower costs and fewer resources for rehabilitation.

Therefore, instruments have been developed in recent years which allow the surgeon to fix the polyaxial screws in the desired position even through a small incision on the patient's body, together with the possibility of implanting the bars in the desired position through these instruments.

In particular, surgical devices have been developed comprising a polyaxial screw provided with a tulip, associated with a threaded shaft, having two elongated rods spaced apart which define a guide channel for access the interior of the tulip itself.

The two rods are advantageously configured to couple in a practical and precise manner with two respective cavities for accommodating an implant device (e.g. a "screwdriver" with a counter-beveled tip at the head of the screw to allow the screw to be screwed into the bone).

At the end of the operation, the implant device is thus removed, and the tulip rods can be removed from the patient's body, e.g. by effraction, leaving only the tulip and the implanted threaded shaft inside the patient's body. However, the Applicant has observed that the elongated rods, once the screw is inserted into the patient's body, tend to approach each other as a result of the pressing pressure exerted by the surrounding tissues, which, by leveraging the connection portions of the rods to the tulip, cause the free ends of the rods to come closer together. In such situations, in addition to partial occlusion of the wound, parts of tissue may be pinched between the two rods or pinched by the coupling between the instruments, causing injuries and lacerations.

The Applicant has thus identified the need to ensure that the rods do not approach each other during use of the device and that the connections between the implant devices and the polyaxial surgical screw are functional and, at the same time, allow the integrity of the device before and during use. Accidental disassembly, e.g. caused by the approach of the rods, could lead to an unwanted extension of the intervention time.

OBJECT OF THE INVENTION

In this context, it is the technical task underlying the present invention to suggest a surgical device which overcomes the drawbacks of the prior art mentioned above.

In particular, it is the object of the present invention to provide a surgical device which allows improving the efficiency of the surgical steps before, during and after the implantation of a polyaxial surgical screw, thus safeguarding the patient's health.

The technical task and the specified objects are substantially achieved by a surgical device comprising the technical features disclosed in one or more of the appended claims.

In particular, the present invention provides a surgical device comprising a polyaxial surgical screw.

The polyaxial surgical screw comprises an internally hollow tulip having a first open end for accessing the interior of the tulip, a second end opposite to the first end, and a side wall developing between the first and second end.

The tulip comprises two elongated rods, which are parallel and mutually spaced apart, each elongated rod protruding from the side wall and extending away from the first end of the tulip in a direction opposite to the second end of the tulip.

The rods define a channel in communication with the first end for accessing the interior of the tulip.

The polyaxial surgical screw further comprises a threaded shaft having a first end defining the screw tip and a second end opposite to the first end, having a ball joint associated with the second end of the tulip to orient the shaft with respect to the tulip itself.

Advantageously, the surgical device comprises a locking unit which can be reversibly mounted on the polyaxial surgical screw.

The locking unit comprises a tubular body which has an inner cavity and is adapted to be fitted about the elongated rods during a configuration of use of the surgical device.

The tubular body has two mutually opposite protrusions which project into the inner cavity and which are configured to face the channel defined between the rods and configured to be interposed between the elongated rods to prevent the mutual removal and approach of the elongated rods during the configuration of use of the surgical device.

By virtue of the locking unit, it is thus possible to keep the two elongated rods of the polyaxial surgical screw at an adequate mutual distance during the surgical steps, thereby defining a passage channel for the insertion of surgical instruments and implantation devices, avoiding pinching of the tissues.

Furthermore, by keeping the two elongated rods in place, it is possible to prevent accidental breakage of the rods.

Once the operation is complete, the locking unit can be simply removed from the polyaxial surgical screw to proceed with the removal of the elongated rods.

The dependent claims, incorporated herein by reference, correspond to different embodiments of the invention.

BRIEF DESCRIPTION OF THE DRAWINGS

Further features and advantages of the present invention will become more apparent from the following indicative and thus non-limiting description of a preferred, but not exclusive, embodiment of a surgical device, as shown in the accompanying drawings, in which:

FIGS. 4 and 4A are a diagrammatic perspective view and a diagrammatic bottom view, respectively, of the locking unit of the surgical device of FIG. 1 in the unlocking position.

DETAILED DESCRIPTION OF PREFERRED EMBODIMENTS OF THE INVENTION

Figure 1:
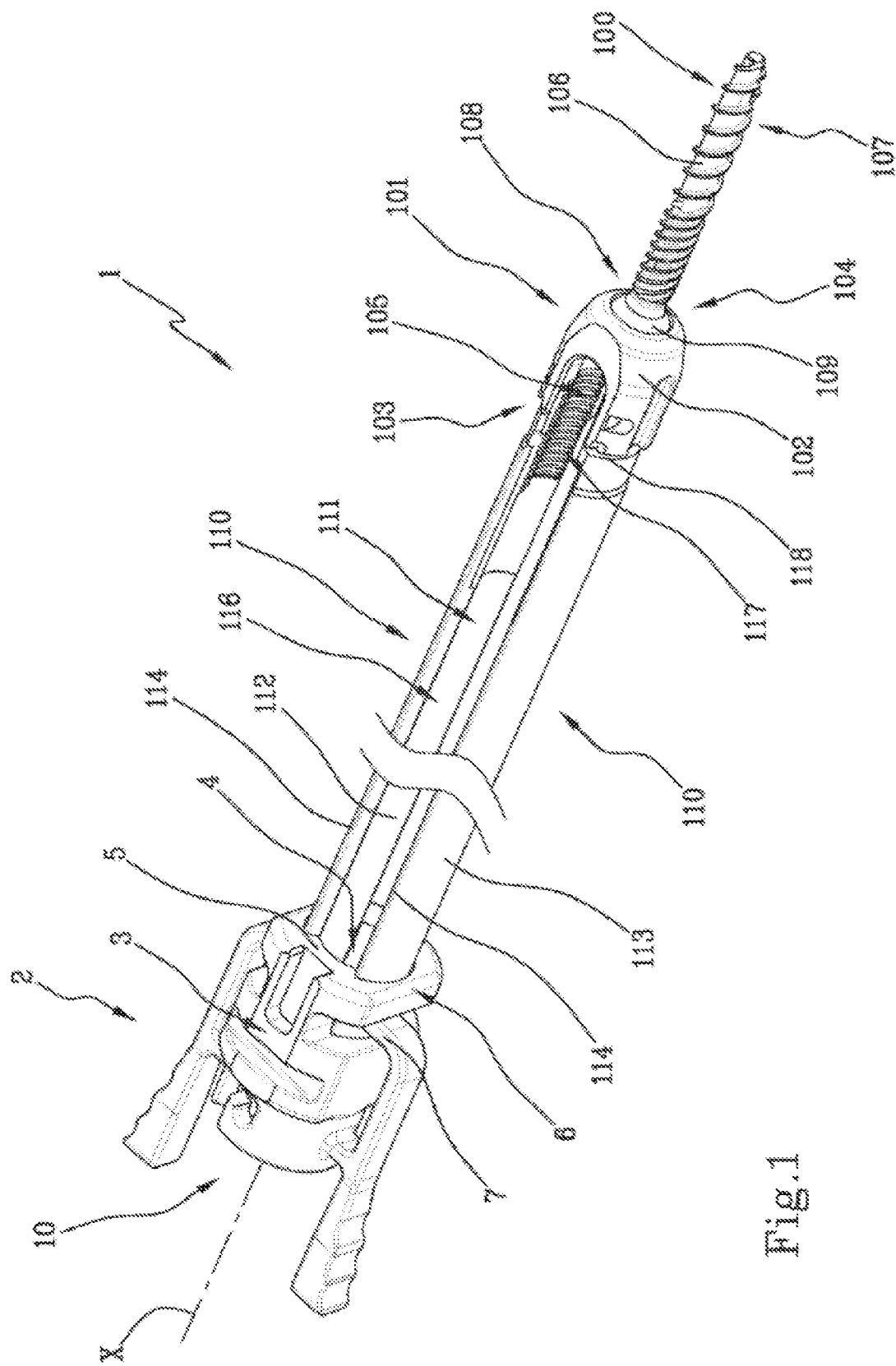
FIG. 1 is a diagrammatic perspective view of the surgical device of the present invention.

With reference to the accompanying figures, a surgical device is indicated by reference numeral 1.

The device 1 comprises a polyaxial surgical screw 100, henceforth screw 100, comprising an internally hollow tulip 101 and defined by a "cup"-shaped side wall 102.

In other words, the side wall 102 has a substantially truncated cone shape and extends from a first open end 103 for accessing the interior of the tulip 101 to a second end 104, which is opposite to the first end. The second end 104 is also open and smaller than the access section of the first end 103. In this configuration, the side wall 102 is preferably tapered and converging towards the second end 104.

The tulip 101 further comprises two through-holes 105 cut through the side wall to accommodate a corrective bar (not shown in the figures because they are not part of the present invention) inside the tulip 101 itself.

In particular, the two openings 105 are arranged on opposite sides to allow the bar to pass through the tulip 101 and along a direction perpendicular to the longitudinal development of the side wall 102.

The openings 105 are developed up to the first end 103 to interrupt the side wall 102 at the first access end 103.

The screw 100 further comprises a threaded shaft 106 with a first end 107 defining the tip of the screw, designed to insert into a bone tissue. A second end 108 equipped with a ball head or ball joint 109 inserted into the second end 104 of the tulip 101 develops on the opposite side of the first end 107.

The ball joint 109 allows the shaft 106, and its longitudinal development axis, to be aligned with the tulip 101.

Advantageously, the tulip 101 further comprises two elongated rods 110 which are parallel and mutually spaced apart. The elongated rods 110 protrude from the side wall 102 and extend from the first end 103 of the tulip 101 in a direction opposite to the second end 104 of the tulip 101 itself.

Advantageously, the rods 110 mutually define a channel 111 in communication with the first end 103 for accessing the interior of the tulip 101.

Preferably, each rod 110 has a "C"-shaped development in cross-section in which a concave inner surface 112 is defined, opposite to a convex outer surface 113.

The inner surfaces 112 face each other and define the aforesaid channel 111. The outer surfaces 113 lie along the same cylindrical plane of development with a circular cross-section.

The two elongated rods 110 thus develop in parallel around a central development axis X, which in FIG. 1 is aligned with the direction of development of the shaft 106 of the screw 100.

Additionally, each rod 110 has two longitudinal edges 114 extending from the first end 103 of the tulip 101 to a terminal end 115 of the rod 110 itself distal from the tulip 101, parallel to the X axis.

In this situation, the longitudinal edges 114 of the rods 110 are facing and mutually spaced apart to define an open area 116 for accessing the aforementioned channel 111.

Therefore, two open zones 116 are created between the two rods 110, which develop along the cylindrical development plane on which the outer surfaces 113 lie. In other words, the X axis defines the central development axis of the ideal cylinder along whose side wall the outer surfaces 113 lie. Preferably, a threading 117 is further provided on the concave inner surfaces 112 of the rods 110 near the tulip 101.

In greater detail, the threading 117 further extends along a cylindrical inner surface 102a of the side wall 102. Preferably, the cylindrical inner surface 102a and the concave inner surfaces 112 are adjacent and seamless. Preferably, the tulip 101 has two weakening lines 118, each extending between an elongated rod 110 and the side wall 102. The weakening lines 118 define a separation zone between the rod 110 itself and the tulip 101, i.e. an area in which, as a result of a deflection of each rod 110 with respect to the tulip 101, it is possible to separate the rods 110 from the rest of the surgical device 1.

For this purpose, the weakening lines 118 consist of grooves extending transversely to the longitudinal development of the rods 110 and cut on the respective outer surfaces 113 of the rods 110.

The grooves thus define a reduction in the thickness of the rod 110 such to be able to make it dissociable from the tulip 101 if it is subjected to bending.

Once the surgical screw 100 has been positioned and correctly engaged in the bone tissue, the rods 110, which are protruding outside the patient's body, are bent by the operator to remove them.

Although these weakening lines 118 can facilitate the detachment of the rods 110 from the tulip 101, at the same time they weaken the connection between the 110 rods and the tulip 101, so that the rods 110 could be brought closer together because they are pressed by the surrounding soft tissue.

The device 1 according to the present invention, however, advantageously comprises a locking unit 2 which can be retrofitted onto the screw 100.

The locking unit 2 comprises a tubular body 3 which has an inner cavity 4 and is adapted to be fitted about the elongated rods 110 during a configuration of use of the device 1.

In particular, the tubular body 3 has two mutually opposite protrusions 5, which project, preferably in a radial manner, into the inner cavity 4.

The protrusions 5 are configured to face the channel 111 defined between the rods 110 and be mutually interposed between the rods 110 themselves to prevent the mutual removal and approach during the configuration of use of the device 1.

In other words, by virtue of the presence of the locking unit 2, it is possible to prevent the rods 110 from inadvertently approaching during the surgical steps in which the screw 100 is inserted into the patient's body.

The protrusions 5 are interposed between the rods 110, keeping them in position even after possible pressing.

The locking unit 2 can be easily mounted and removed from screw 100 to be used only when necessary.

It is apparent from the above that locking unit 2 is particularly advantageous when weakening lines 118 are present so that the protrusions 5 of the tubular body 3 prevent the rods 110 from being able to approach as a result of a lever applied by the surrounding soft tissues about the weakening lines 118.

Preferably, the tubular body 3 has two grooves 6 which are mutually opposite and interposed between the two protrusions 5. The grooves 6 are designed to accommodate the rods 110 at least partially to prevent the rotation of the tubular body 3 about the rods 110.

In other words, the inner cavity 4 defines two grooves 6 alternating between their respective protrusions 5, so that the longitudinal edges 114 of each rod 110 are confined in the radial space of a respective groove 6 preventing any rotation of the tubular body 3 (and more in general of the locking unit 2) about the X axis.

Preferably, in the embodiment shown in the figures, the grooves 6 have a dovetail-shaped geometry, which advantageously prevents both the approach of rods 110 and the rotation of the tubular body 3 at the same time.

Figure 2:
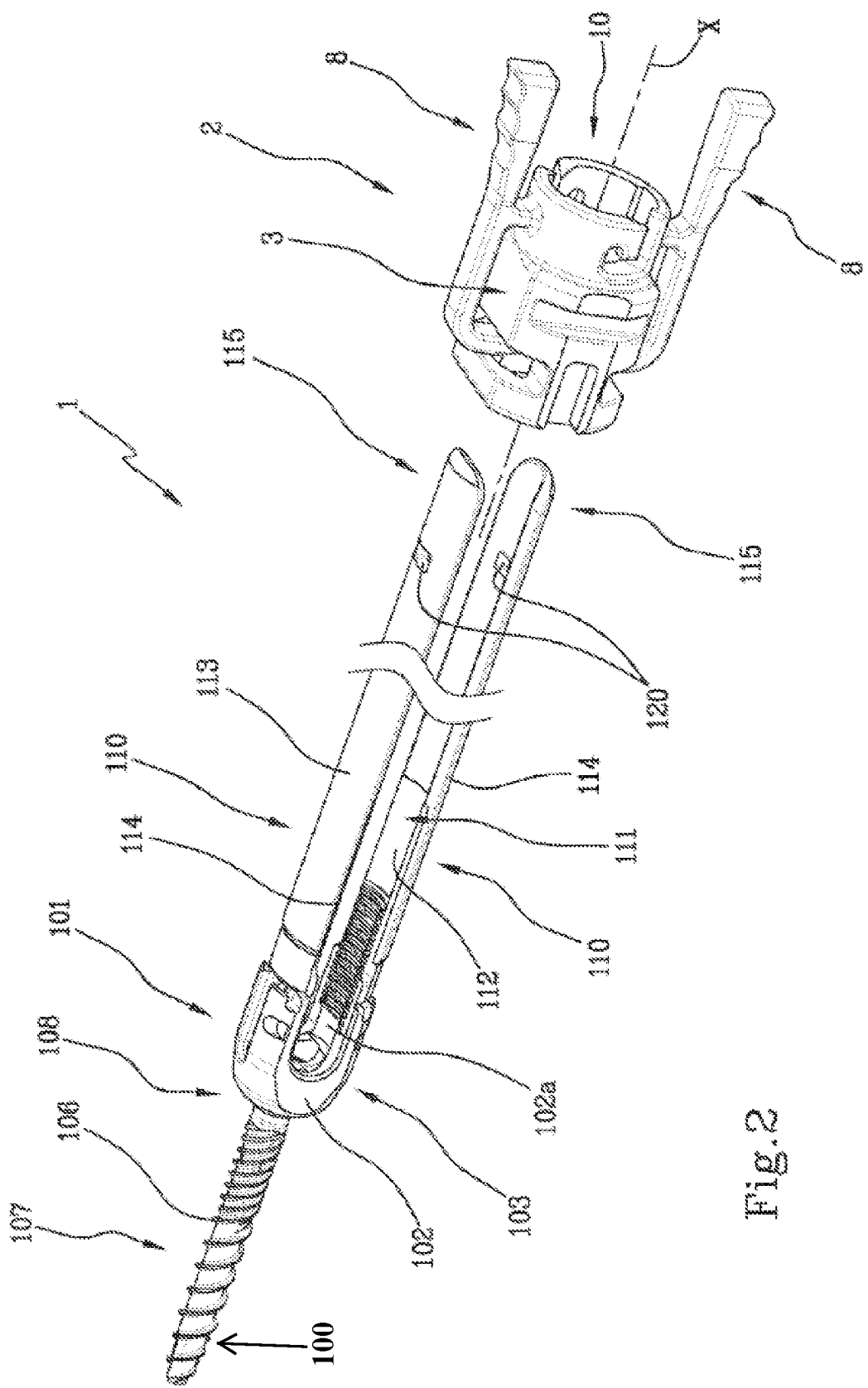
FIG. 2 is a diagrammatic perspective view of the surgical device in FIG. 1, FIGS. 3 and 3A are a diagrammatic perspective view and a diagrammatic bottom view of the locking unit of the surgical device in FIG. 1 in the locking position.

With reference to FIG. 2, the rods 110 preferably have respective through-holes 120 at their terminal ends 115. Furthermore, the locking unit 2 preferably comprises a pair of locking pins 7 (clearly visible in FIGS. 3A and 4A) connected to said tubular body 3 which can be switched during the configuration of use between a locking position (shown in FIGS. 3-3A), where they are inserted into the through-holes 120, thus preventing the axial sliding of tubular body 3 with respect to the rods 110, and an unlocking position (shown in FIGS. 4-4A) in which they are disconnected from the through-holes 120.

In other words, when the locking unit 2 is mounted on the screw 100, fitting the tubular body 3 on the rods 110, the locking pins 7 are easily and effectively switched from the locking position (in which they are preferably arranged during a non-assembled configuration of device 1 in which the locking unit 2 is not used) to the unlocking position to be fitted on rods 110; the locking pins 7 are then moved from the unlocking position to the locking position to keep the rods 110 in position and prevent any rotation of the tubular body 3 about the screw 100.

Preferably, the locking unit 2 further comprises a pair of arms 8 connected to the tubular body 3; each arm 8 has a first end 8a on which a respective locking pin 7 is made and a second end 8b defining a gripping portion of the locking unit 2. The arms 8 can be operated in rotation around respective fulcrums F (arranged along parallel axes of oscillation Y, preferably perpendicular to the X axis) of the tubular body 3 to approach the gripping portions 8b closer and to move the locking pins 7 (FIGS. 4-4A) and vice versa (FIGS. 3-3A) to switch the locking pins 7 respectively between the locked and unlocking position and vice versa.

In other words, by grasping the locking unit 2 with at least two fingers, the surgeon can conveniently press the gripping portions 8b by levering the fulcrums F to remove the locking pins 7 and thus be able to fit the tubular body 3 onto the rods 110 (as diagrammatically shown by the arrows in FIG. 4A).

When the tubular body 3 is arranged along the development of the rods 110 so that the locking pins 7 are aligned with the through-holes 120, the locking pins 7 can then be inserted into the respective through-holes 120 so that the locking element 2 is firmly secured to screw 100 in the locking position. In other words, by virtue of a simple lever mechanism, it is possible to tie the locking element 2 with screw 100 so that the rods 110 are prevented from approaching one another.

Furthermore, according to a possible embodiment of the present invention, preferably fulcrums F can be associated with torsional springs (not shown). As shown in the embodiment in the accompanying figures, preferably the locking pins 7 are released into the grooves 6 when they are arranged in the locking position.

Figure 3A:
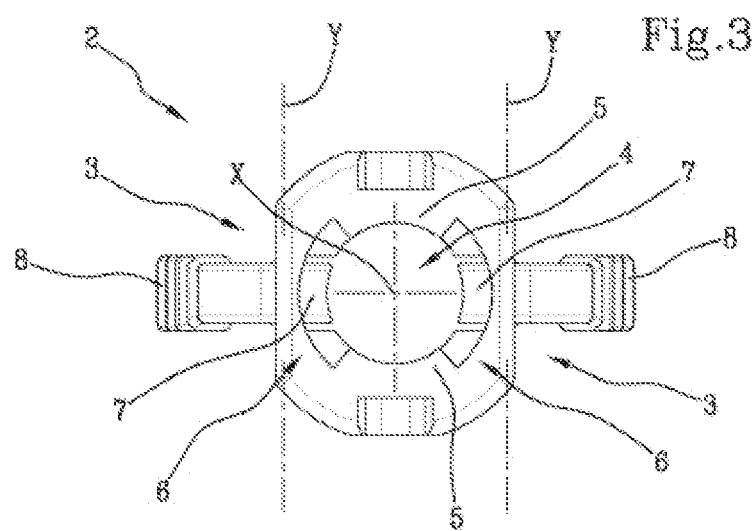
Figure 3:
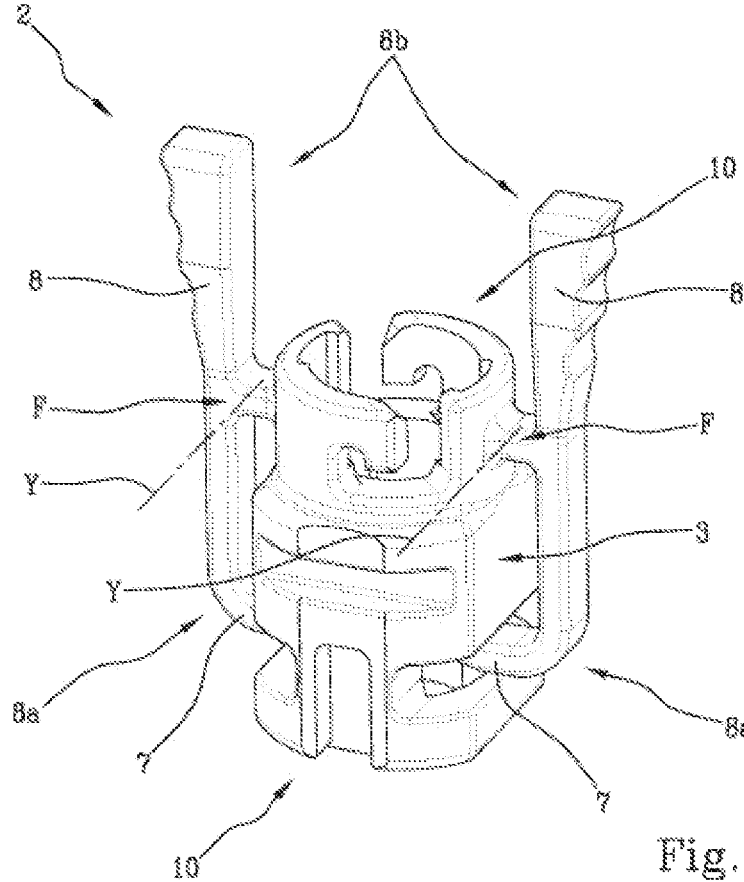

Even more preferably, the locking pins 7 have a counter-shape portion of contact with rods 110 with respect to the outer surfaces 113 of rods 110 (FIG. 3A).

Preferably, the locking unit 2 comprises a coupling portion 10 connected to the tubular body 3 and configured to couple the locking unit 2 to a surgical instrument, which is not shown in the attached figures because it is not part of the invention.

In other words, the coupling portion 10 defines the direct connection interface between device 1 and a surgical instrument, thus facilitating any corrective maneuvers (e.g. compression and distraction) and keeping channel 111 free.

In particular, the coupling portion 10 defines an extension of the inner cavity 4 of the tubular body 3 adapted to be placed on the opposite side to the tulip 101.

Preferably said coupling portion 10, during the configuration for use of the device 1, is arranged in a position distal from the tulip 101 to the tubular body 3.

Furthermore, the coupling portion 10 preferably features a bayonet-type connection system to make the coupling with the surgical instruments practical, stable and universal.

By virtue of the coupling portion 10, it is possible to achieve the safe and guided coupling of the surgical instruments which will fit into the channel 111. Once the locking unit 2 is mounted on the screw 100, the coupling portion 10 is arranged coaxially with respect to the X axis, thus simplifying the centering of the surgical instruments.

Finally, the locking unit 2 is preferably of the disposable type, being supplied sterilized, and can be made of both plastic and metal material.

The present invention thus achieves the suggested objects, overcoming the drawbacks described with reference to the prior art and providing the user with a surgical device 1 equipped with a special accessory (locking unit 2) which allows the connection between the two elongated rods 110 of the tulip 101 and allows the agile use of other dedicated instruments at the same time to complete the surgery.

The mechanism works by virtue of the geometric fittingness between device 1 and instrument avoiding the disjointed movement of the rods 110 (in particular their approaching) and preventing their accidental breakage.

The device 1 allows a simplified and fluid surgical procedure by preventing injury and tissue tearing due to any approach or breakage of the rods 110 while keeping the channel 111 free of obstructions during the surgical steps.

The invention claimed is:

1. A surgical device comprising:
a polyaxial surgical screw comprising:
an internally hollow tulip having a first open end for accessing an interior of the tulip, a second end opposite to the first end, and a side wall developing between the first and second end, wherein said tulip comprises two elongated rods which are parallel and mutually spaced apart, each elongated rod protruding from the side wall and extending away from the first end of the tulip in a direction opposite to the second end of the tulip, said rods defining a channel in communication with the first end for accessing the interior of the tulip; and
a threaded shaft having a first end defining a screw tip and a second end opposite to the first end having a ball joint associated with the second end of the tulip to orient said shaft with respect to the tulip itself,
wherein the surgical device further comprises a locking unit which can be reversibly mounted on said polyaxial surgical screw, wherein said locking unit comprises a tubular body which has an inner cavity and is adapted to extend around said two elongated rods during a configuration of use of the surgical device, said tubular body having two mutually opposite protrusions which project into said inner cavity,
said protrusions being configured to face the channel defined between said rods and be interposed between said elongated rods to prevent mutual removal and approach of said elongated rods during the configuration of use of the surgical device;
wherein said rods have respective through holes at respective terminal ends of said rods, and wherein said locking unit comprises a pair of locking pins connected to said tubular body which can be switched during the configuration of use between a locking position, in which they are inserted into said through holes preventing axial sliding of the tubular body with respect to the rods, and a releasing position in which they are disconnected from the through holes;
wherein said locking unit comprises a pair of arms connected to said tubular body, each arm having a first end on which a respective locking pin is made and a second end disposed radially outwardly from the tubular body, the second end defining a gripping portion of the locking unit, the gripping portion comprising a plurality of indentations formed on an outer surface of the gripping portion, said arms being operable in rotation about respective fulcrums of the tubular body to approach the gripping portions and to move the locking pins respectively between the locking position and the releasing position and vice versa to switch the locking pins.

2. The surgical device according to claim 1, wherein each rod has a substantially "C"-shaped development in cross-section and wherein the rods have mutually facing respective concave inner surfaces and respective convex outer surfaces opposite to the concave surfaces, said outer surfaces lying along a respective circular-section cylindrical plane of development; wherein said tubular body has two mutually opposite grooves interposed between the two protrusions, said grooves being shaped to accommodate said rods at least partially to prevent rotation of the tubular body about the rods.

3. The surgical device according to claim 2, wherein said locking pins are released into the grooves when they are arranged in the locking position.

4. The surgical device according to claim 1, wherein said locking unit comprises a coupling portion connected to said tubular body and configured to couple said locking unit to a surgical instrument.

5. The surgical device according to claim 4, wherein said coupling portion, during the configuration for use of the device, is arranged in a position distal from the tulip to the tubular body.

6. The surgical device according to claim 4, wherein said coupling portion has a bayonet-type connection system.

7. The surgical device according to claim 1, wherein at least a portion of the tubular body is annular shaped.

8. The surgical device according to claim 1, wherein the outer surface of the gripping portion further comprises a first gripping end and a second gripping end spaced apart from the first gripping end, the first gripping end being closer to the fulcrum than the second gripping end,
wherein the outer surface of the gripping portion is formed at an angle such that, in the locking position, a second gripping end is disposed radially outwardly from the inner cavity of the locking unit further than the first gripping end.

* * * * *